United States Patent [19]

Shannon, Jr. et al.

[11] Patent Number: 5,123,425
[45] Date of Patent: Jun. 23, 1992

[54] OBSTRUCTIVE SLEEP APNEA COLLAR

[75] Inventors: John L. Shannon, Jr., Orono; Bruce R. Bowman, Eden Prairie, both of Minn.

[73] Assignee: EdenTec, Eden Prairie, Minn.

[21] Appl. No.: 578,150

[22] Filed: Sep. 6, 1990

[51] Int. Cl.$^5$ .................. A61F 5/56; A61B 5/08; A61B 5/04
[52] U.S. Cl. .................. 128/848; 128/724; 128/733
[58] Field of Search .............. 128/846, 848, 859, 860, 128/724, 733, 773, 774, 777, 419 R; 340/573, 575, 626, 665, 668

[56] References Cited

U.S. PATENT DOCUMENTS

| | | | |
|---|---|---|---|
| 2,999,232 | 9/1961 | Wilson | 340/575 |
| 3,032,029 | 5/1962 | Cunningham | 128/732 |
| 3,480,010 | 11/1969 | Crossley | 128/848 |
| 3,593,703 | 7/1971 | Gunn | 128/392 |
| 3,696,377 | 10/1972 | Wall | 340/575 |
| 3,998,209 | 12/1976 | Macuaugh | 128/148 |
| 4,220,142 | 9/1980 | Rosen et al. | 128/848 |
| 4,304,227 | 12/1981 | Samelson | 128/848 |
| 4,440,160 | 4/1984 | Fischell | 128/846 |
| 4,593,686 | 6/1986 | Lloyd et al. | 128/848 |
| 4,669,477 | 6/1987 | Ober | 128/777 |
| 4,715,367 | 12/1987 | Crossley | 600/27 |
| 4,830,008 | 5/1989 | Meer | 128/721 |

OTHER PUBLICATIONS

"Effects of Electrical Stimulation of the Genioglossus on Upper Airway Resistance in Anesthesized Dogs", Miki et al.
"Effects of Submental Electrical Stimulation During Sleep on Upper Airway Patency in Patients with Obstructive Sleep Apnea", Miki et al.
"Diaphragm Pacing: Present Status", Glenn.

Primary Examiner—Robert A. Hafer
Assistant Examiner—Michael Brown
Attorney, Agent, or Firm—James R. Shay; John L. Rooney

[57] ABSTRACT

A system for the treatment of obstructive sleep apnea packaged in a collar which can be worn by a patient without any special preparation. The collar is adjustable using a fastener such as hook and latch, to accommodate variations in neck size. The collar is properly oriented using variations in physical shape and/or color. An optional feedback system permits the patient to readily verify proper orientation.

The collar contains at least one sensor to monitor functioning of the respiratory system of the patient.

The output of the sensor(s) is processed by battery powered electronics located within or in proximity to the collar. When an apnea episode is detected, the electronics module generates bursts of pulsatile current which are conducted to electrodes located on and positioned by the collar or in proximity to the collar. The pulsatile current is transferred transcutaneously from the electrodes to the nerves innervating the genioglossus and other muscle groups causing them to contract or through afferent excitation causing reflexive contraction of these muscles to thereby clear the upper air passageway.

15 Claims, 7 Drawing Sheets

OBSTRUCTIVE SLEEP APNEA COLLAR

BACKGROUND OF THE INVENTION

1. Field of the Invention

The present invention relates generally to medical devices, and more particularly, relates to transcutaneous electrical stimulation treatment of obstructive sleep apnea.

2. Description of the Prior Art

Sleep apnea is a medical condition which effects a large segment of the population. It exists in several forms. Perhaps the most dangerous, called central apnea, is associated with a lack of central drive to breath or with a disruption of the neural pathways from the brain to the diaphragm muscles. Research has been progressing for some time with one mode of treatment being electrical stimulation of the phrenetic nerve, thereby controlling function of the diaphragm. William W. L. Glenn describes the nature of this research in "Diaphragm Pacing: Present Status" in Pace, Volume 1, pages 357-370, July - September 1978.

A second form of sleep apnea, and of most concern to the present invention, is that which obstructs the upper air passageways. This condition has numerous deleterious results including disturbance of the patient and sleep partner and loss of effectiveness of the sleep process resulting in excessive patient fatigue. Long term effects include hypertension and cardiac problems.

The simplest forms of treatment for upper air passage obstructive sleep apnea involve mechanical constraints. U.S. Pat. No. 4,304,227 issued to Samelson describes such a device. Various surgical techniques are also employed including tracheostomy.

Perhaps the most common technique is through the use of systems which detect the obstructive condition and alert the patient to the problem in some fashion. Examples of this type of system include: U.S. Pat. No. 2,999,232 issued to Wilson; U.S. Pat. No. 3,032,029 issued to Cunningham; U.S. Pat. No. 3,480,010 issued to Crossley; U.S. Pat. No. 3,593,703 issued to Gunn et al.; U.S. Pat. No. 3,696,377 issued to Wall; U.S. Pat. No. 3,998,209 issued to Macvaugh; U.S. Pat. No. 4,220,142 issued to Rosen et al.; and U.S. Pat. No. 4,593,686 issued to Lloyd et al. These devices employ a variety of techniques, but each tends to be based upon detection of the condition and producing an alarm. Unfortunately, the alarm may rouse the patient to the extent that patient's sleep is disturbed, thereby exacerbating the very problem caused by the apnea episode.

Recently, research has been conducted which shows that the obstruction within the upper air passageway may be cleared with electrical stimulation. Two articles, herein incorporated by reference, describing this research may be found in American Review of Respiratory Disease Volume 140, 1989 at pages 1279 through 1289. The first article is "Effects of Electrical Stimulation of the Genioglossus on Upper Airway Resistance in Anesthetized Dogs", by Hiroshi Miki et al. The second article is "Effects of Submental Electrical Stimulation during Sleep on Upper Airway Patency in Patients with Obstructive Sleep Apnea", also by Hiroshi Miki et al.

U.S. Pat. No. 4,830,008 issued to Meer discusses an implantable system for treatment of obstructive sleep apnea using electrical stimulation. The implanted sensor(s) are used to sense inspiratory effort and stimulate the nerves of the upper airway in synchrony with the respiration cycle. Because upper airway stimulation may not be required for each inspiratory effort, Meer proposes an embodiment which also senses muscular activity in the upper airway to inhibit stimulation for certain respiratory cycles. However, it is not clear that the added complexity and morbidity of an implantable system are justified in the absence of evidence that stimulation only during the inspiratory effort is either necessary or sufficient.

SUMMARY OF THE INVENTION

The present invention overcomes the disadvantages of the prior art systems by providing an external device for the effective treatment of obstructive sleep apnea using a collar which may be easily and properly attached by the patient. The collar senses the onset of an apnea episode and automatically applies electrical signals which either stimulates the patient's muscles to clear the obstruction or stimulates a reflexive response of causing the patient's muscles to clear the obstruction. Because the device is worn externally, it does not require the expense and risk associated with an implant procedure. Because the electrical stimulation is supplied with little sensation, the effectiveness of sleep is preserved.

The collar is readily attachable using hook and latch or other suitable fasteners. Means located on the collar ensure proper placement of the sensor and stimulation electrodes. The positioning means can take the form of variations in shape or color of the collar. The collar is self contained; and therefore, promotes patient compliance through ease of use. It may be made in disposable form to ensure ease of manufacture.

A sensor located on or near the collar is used to determine the onset of an apnea episode. Proper functioning of the respiratory system may be monitored directly in the form of air flow, direct or indirect blood gas measurements (such as pulse oxygen saturation), or indirectly via breath or snoring sounds, breath temperature, pressure sensors, thoracic impedance, strain gauges, or airway resistance. The output of the sensor is conditioned and interpreted, and used to determine whenever an apnea event is initiated. A stimulation signal is generated which is coupled to transcutaneous neuro muscular electrodes. These stimulation signals cause the genioglossus and related muscle groups to contract thereby clearing the upper air passageway.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
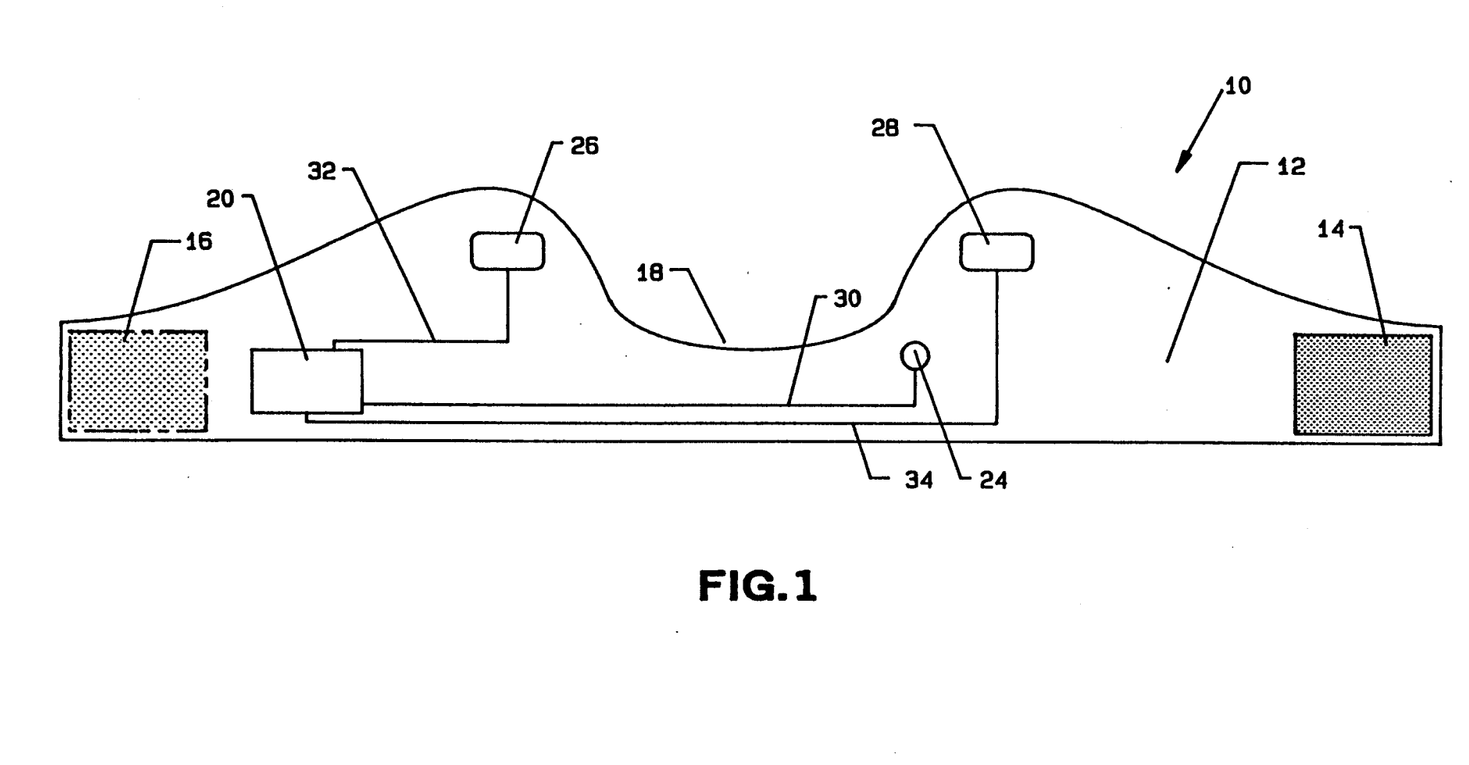
FIG. 1 is a plan view of an obstructive sleep apnea collar.

FIG. 1 is a plan view of an obstructive sleep apnea collar 10 of the present invention. The main substrate 12 is of a flexible material suitable for wrapping about the patient's neck. Preferably main substrate 12 is of a porous woven material which permits the collar to "breathe". Main substrate 12 is fastened about the neck of the patient using convenient fasteners such as hook 14 and latch 16 (see also FIGS. 4 and 5). Preferably, hook 14 and latch 16 are sufficiently wide to permit adjustment to necks of varying sizes.

It is important that collar 10 be properly positioned when attached to the neck of the patient t ensure that the components located on main substrate 12 are properly positioned. In the preferred embodiment, this is accomplished with chin notch 18 which accommodates the chin of the patient. In this way, the patient can easily feel that collar 10 is properly positioned.

Sensor 24 is used to determine the onset of an apnea episode. In the preferred embodiment, this is a microphone or motion sensor which generates an electrical signal corresponding to the presence of breath or snoring sounds. Other sensors which may be used include an oximeter to measure the percentage of oxygen saturation of the blood, an airflow sensor, an airway resistance sensor, a strain gauge, or using an impedance pneumography. Sensor 24 is fixedly mounted to main substrate 12 such that when collar 10 is positioned using chin notch 18, sensor 24 is properly located for its monitoring function. Sensor 24 is electrically coupled to electronic module 20 using cable 30. Electronic module 20 contains the circuitry to process the sensor output and generate stimulation signals as required. Electronic module 20 is discussed in more detail below.

The electrical stimulation signals generated by electronic module 20 are coupled to electrode 26 and electrode 28 via cable 32 and cable 34, respectively. Electrodes 26 and 28 are similar to commercially available muscle stimulation electrodes. Each is fixed to main substrate 12 such that it will be properly located to stimulate the genioglossus and related muscle groups when collar 10 is in position.

Figure 2:
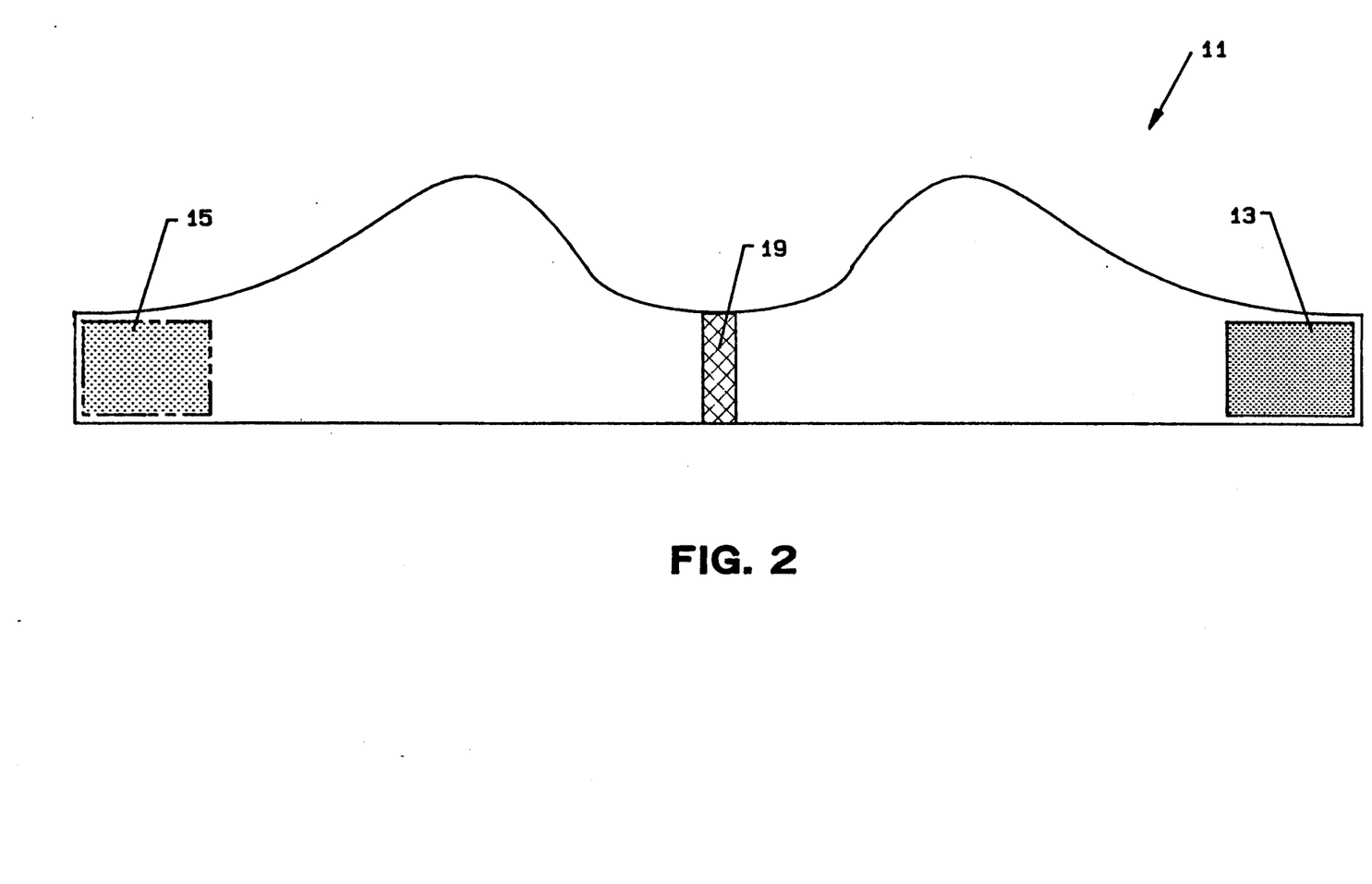
FIG. 2 is an obstructive sleep apnea collar showing an alternative positioning means.

FIG. 2 shows obstructive sleep apnea collar employing a first alternative positioning means. Collar 11 has a color stripe 19 which the patient positions over his trachea. Collar 11 is constructed such that color stripe 19 is located the proper distance from hook 13 and latch 16.

Figure 3:
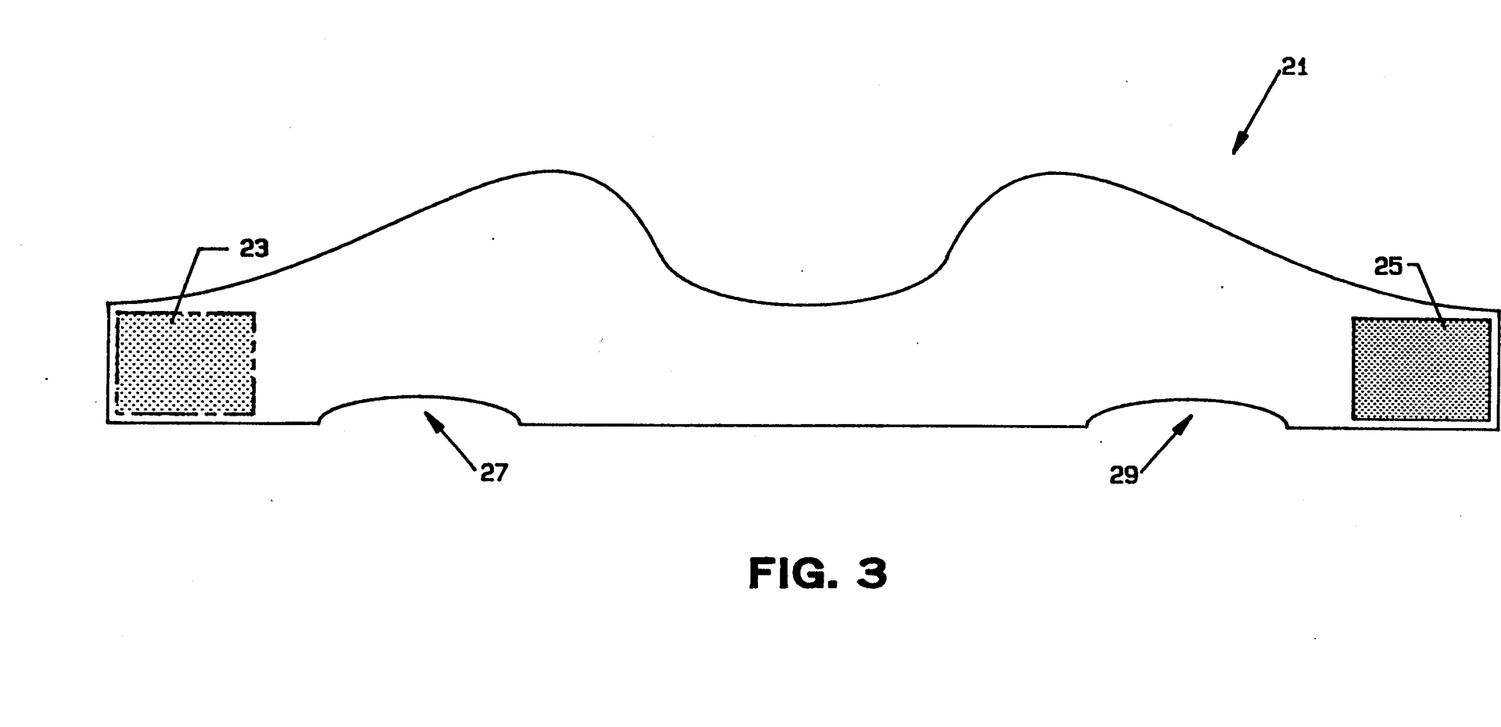
FIG. 3 is an obstructive sleep apnea collar showing a second alternative positioning means.

FIG. 3 is a plan view of obstructive sleep apnea collar 21 using a second alternative positioning means. Collar 21 employs shoulder notches 27 and 29 which are spaced appropriately from hook 23 and latch 25. Unlike chin notch 18 (see also FIG. 1), shoulder notches 27 and 29 are located along the bottom surface of collar 21.

Figure 4:
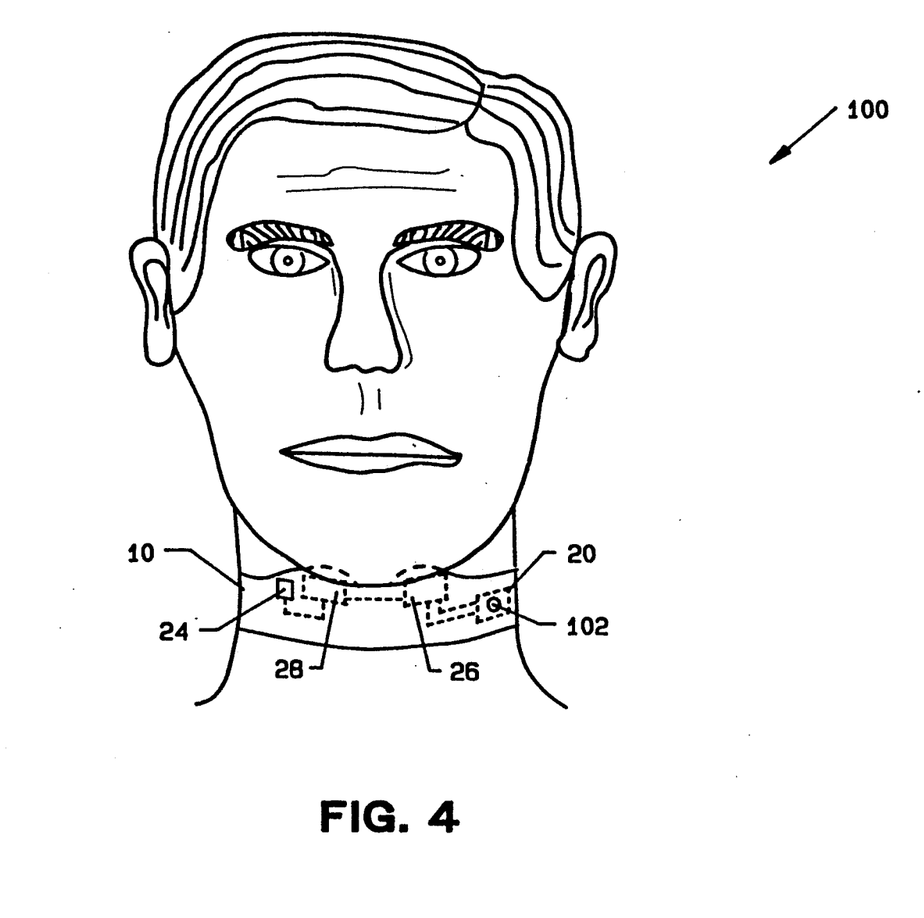
FIG. 4 is a frontal view of a patient wearing an obstructive sleep apnea collar.

FIG. 4 is a frontal view of patient 100 with obstructive sleep apnea collar 10 properly positioned for treatment. All other components are as previously described.

Figure 5:
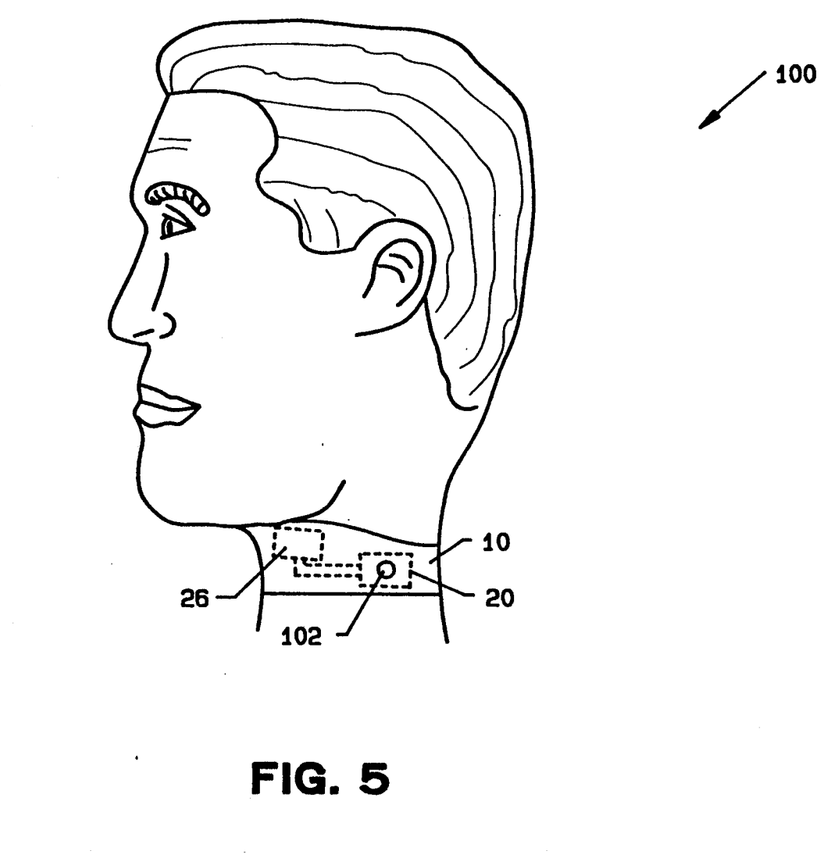
FIG. 5 is a side view of a patient wearing an obstructive sleep apnea collar.

FIG. 5 is a side view of patient 100 with obstructive sleep apnea collar 10 in position. Also shown is optional feedback positioning button 102. The use of button 102 provides patient 100 with positive verification that collar 10 has been properly positioned. Button 102 is depressed by patient 100 to activate the muscle stimulation signal from electronic module 20. If collar 10 is properly positioned, patient 100 will notice a contraction of the muscles associated with his upper air passageway.

Figure 6:
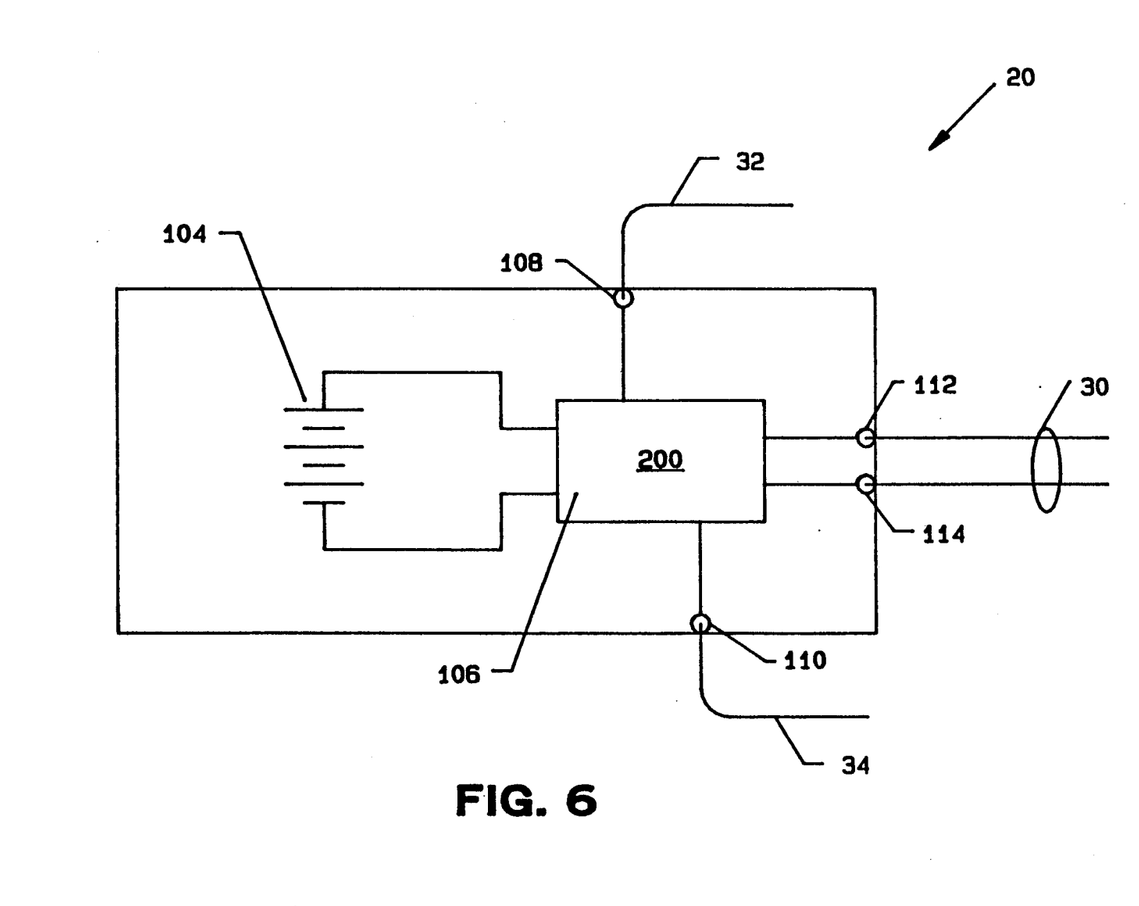
FIG. 6 is an overall view of the electronic module of the obstructive sleep apnea collar; and, FIG. 7 is a block diagram of the electronic circuit of the obstructive sleep apnea collar.

FIG. 6 is a schematic view of electronic module 20 showing its major components. Electronic circuit 200 is powered by primary battery 104 which may or may not be included in the collar. Electronic circuit 200 is preferably a custom integrated circuit, but more probably is a hybrid.

Electronic circuit 200 may or may not be included in the collar and has one input cable 30 from sensor 24 and two output cables 32 and 34 coupled to electrodes 26 and 28, respectively (see also FIG. 1). Referring again to FIG. 6, input cable 30 terminates at terminals 112 and 114. Similarly, output cable 32 terminates at terminal 108 and output cable 34 terminates at terminal 110.

Figure 7:
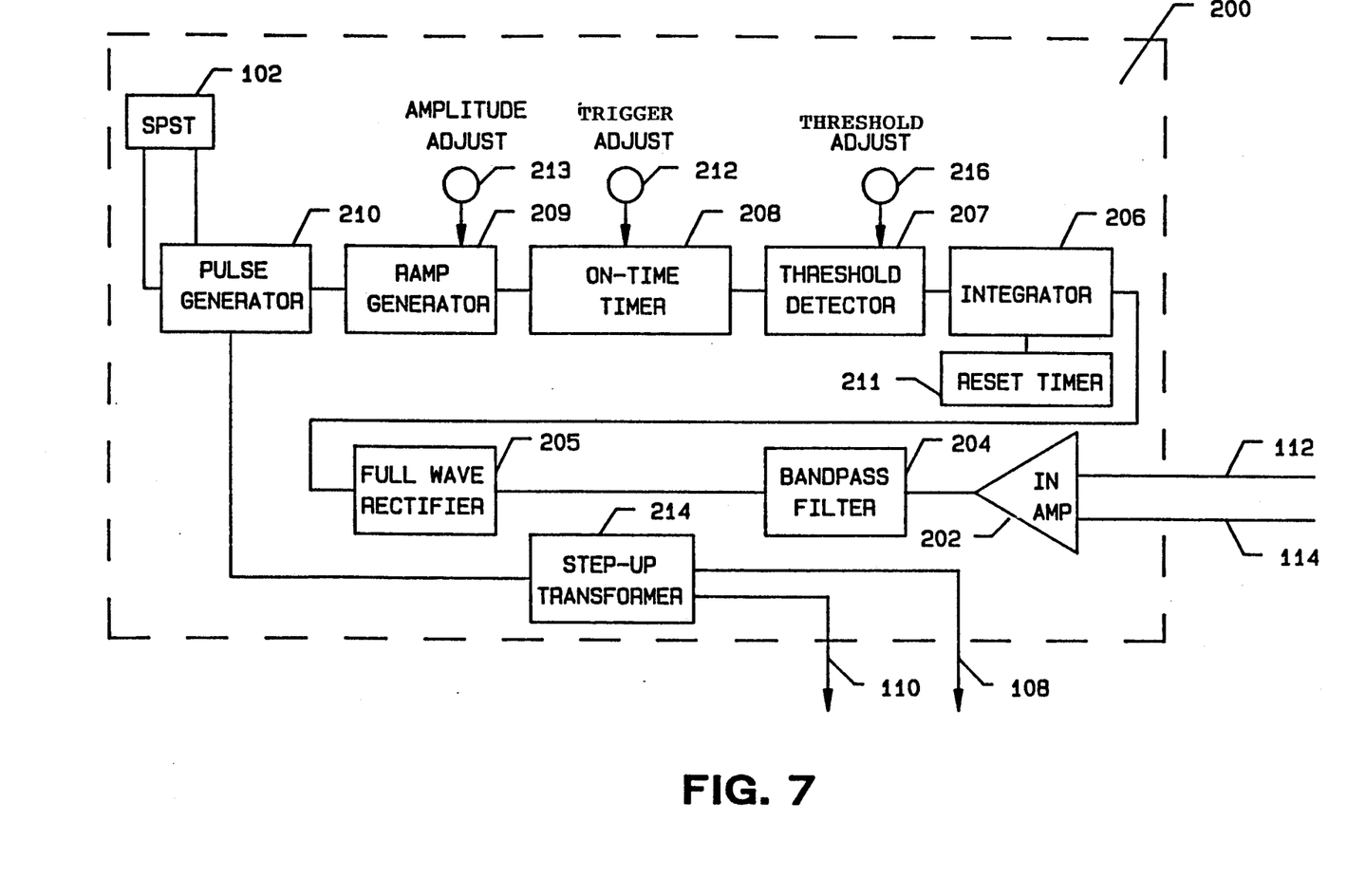

FIG. 7 is a block diagram of electronic circuit 200. Each of the components of electronic circuit 200 is readily available in commercial form. Cable 30 from sensor 24 (see also FIGS. and 6), transfers the sensor signal via terminals 112 and 114 to In amp 202, which provides initial amplification. Bandpass filter 204 filters the amplified sensor signal to obtain the desired pass band. For sensor 24 as a breath or snoring activity sensor, for example, the desired passband of bandpass filter 204 is approximately from 20 to 200 hertz.

The filtered signal is presented to full wave rectifier 205 and then to integrator 206 which integrates the signal over the appropriate time. For sensor 24 as an audio sensor, one-third of a second is an appropriate integration time as determined by reset timer 211. The output of integrator 206 is a level representing the integrated sensor signal. This level is presented to threshold detector 207 having the threshold value set by threshold adjust 216. This ensures that whenever the integrated level exceeds the threshold set by threshold adjust 216, a signal is set to on-time timer 208 which initiates a ramp signal from ramp generator 209 for the duration as set by trigger adjust 212.

Stimulation signals are produced by pulse generator 210 having an amplitude set by the output of ramp generator 209. The amplitude of these pulses is set by amplitude adjust 213. The on-set of these pulses is slowly ramped up in amplitude by ramp generator 209. These signals are appropriate to stimulate contraction of the genioglossus and related muscle groups. The preferred stimulation frequency is 20 to 60 pulses per second. On-time timer 208 ensures that the stimulation bursts are at least a predetermined minimum duration. As explained above, button 102 is a single pole/single throw push button used to manually activate pulse generator 210. This manual activation permits patient 100 to verify proper positioning of collar 10.

The output of pulse generator 210 is coupled to step-up transformer 214 which provides the appropriate voltage necessary to drive electrodes 26 and 28 via cables 32 and 34 respectively.

Having thus described the preferred embodiments of the present invention, those of skill in the art will be readily able to apply the teachings found herein to yet other embodiments without departing from the scope of the claims hereto attached.

We claim:

1. An apparatus for treating obstruction of an upper air passageway of a patient comprising:

a. means for sensing the onset of an obstructive sleep apnea episode;
b. means coupled to said sensing means for generating muscle stimulating signals which directly produce contraction of muscle tissue of said upper air passageway;
c. electrode means coupled to said generating means for transcutaneously transferring said muscle stimulating signals directly to said muscle tissue of said upper air passaageway to clear said upper air passageway of said patient; and
d. means attached to said sensing means, said generating means, and said electrode means for maintaining said sensing means, said generating means, and said electrode means in proximity with said patient.

2. An apparatus according to claim further comprising means coupled to said maintaining means for positioning said maintaining means with respect to said patient.

3. An apparatus according to claim 2 wherein said maintaining means further comprises a collar.

4. An apparatus according to claim 3 wherein said sensing means further comprises an audio sensor.

5. An apparatus according to claim 3 wherein said sensing means further comprises a strain gauge.

6. An apparatus according to claim 3 wherein said sensing means further comprises an oximeter.

7. An apparatus according to claim 3 wherein said sensing means further comprises an air flowmeter.

8. An apparatus according to claims 2, 3, 4, 5, 6, or 7 wherein said positioning means further comprises a unique shape of said maintaining means for positioning said maintaining means.

9. An apparatus according to claim 8 wherein said unique shape further comprises a chin notch.

10. An apparatus according to claim 9 further comprising means coupled to said generating means for verifying proper placement of said maintaining means.

11. An apparatus according to claim 8 wherein said unique shape further comprises at least one shoulder notch.

12. An apparatus according to claim 11 further comprising means coupled to said generating means for verifying proper placement of said maintaining means.

13. An apparatus according to claim 8 further comprising means coupled to said generating means for verifying proper placement of said maintaining means.

14. An apparatus according to claims 2, 3, 4, 5, 6, or 7 wherein said positioning means further comprises a unique color.

15. An apparatus according to claim 14 further comprising means coupled to said generating means for verifying proper placement of said maintaining means.

* * * * *